United States Patent [19]

Berner

[11] 4,355,976
[45] Oct. 26, 1982

[54] AMALGAM CARRIER WITH UNITARY SPRING LEVER MEMBER

[75] Inventor: Vincent A. Berner, Middleton, N.J.

[73] Assignee: Pennwalt Corporation, Philadelphia, Pa.

[21] Appl. No.: 306,993

[22] Filed: Sep. 30, 1981

[51] Int. Cl.$^3$ ............................................. A61C 3/08
[52] U.S. Cl. ..................................................... 433/83
[58] Field of Search ............................. 433/83, 80, 90

[56] References Cited

U.S. PATENT DOCUMENTS 3,091,860 6/1963 Baughan ................................ 433/90
4,106,199 8/1978 Gaccione ............................... 433/83

Primary Examiner—Robert Peshock

[57] ABSTRACT

Present day amalgam carriers include a separate spring member for urging the dispensing lever to its original position after serving to dispense the amalgam or restorative material into a prepared cavity, for example. Fracturing of the spring member occurs periodically and replacement thereof in the carrier, even if replaceable, is a time-consuming and frustrating operation and demands digital dexterity. The present invention provides an improved amalgam carrier wherein the spring and dispensing lever form a unitary member which requires infrequent replacement, if any, and when so replaced, or any other replaceable component of the carrier, may be done with comparative ease.

8 Claims, 8 Drawing Figures

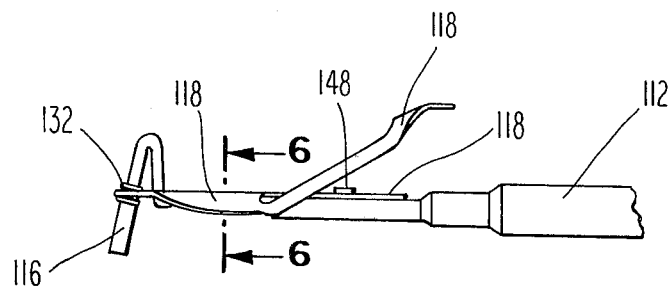
Fig. 4
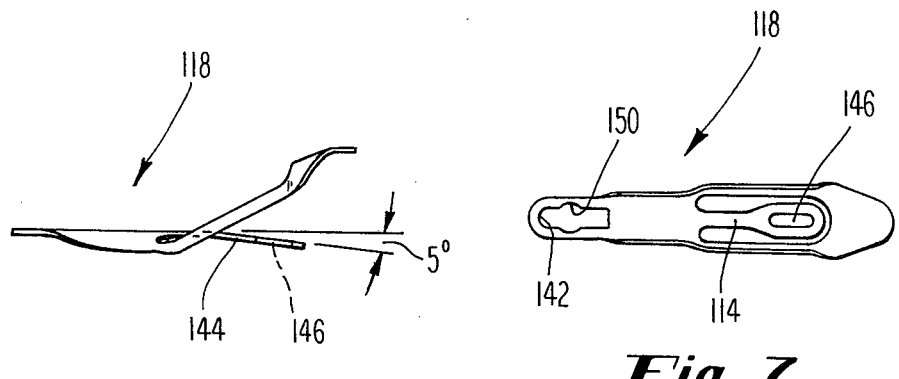
Fig. 5
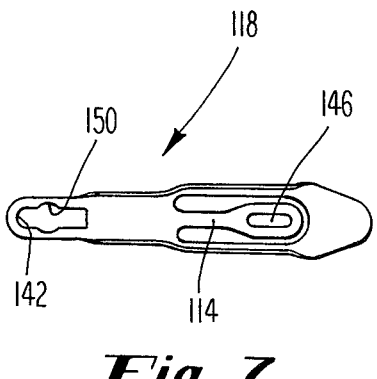
Fig. 7
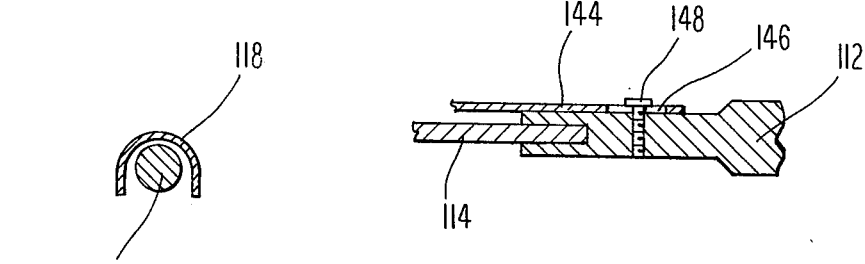
Fig. 6
Fig. 8

4,355,976

AMALGAM CARRIER WITH UNITARY SPRING LEVER MEMBER

STATEMENT OF THE INVENTION

This invention relates to an amalgam carrier and more particularly to such a device having an unitary spring lever member.

BACKGROUND AND SUMMARY OF THE INVENTION

Amalgam is an alloy of mercury with another metal or metals, usually silver, and is used extensively for dental fillings. The amalgam is mixed immediately prior to filling a prepared cavity. Many present day amalgam carriers employ a dispensing lever which, when depressed, causes an end of a plunger rod to slide through a barrel member when the barrel member, containing the amalgam, is held against a cavity surface. Depressing the lever transfers all or a portion of the amalgam in the barrel into the cavity. A separate leaf-type spring cooperating between the lever and carrier handle returns the lever to its original position. The ejected amalgam is packed into the cavity and carved by means well known. A small quantity of amalgam is usually transferred to the cavity at any one time in order that the dentist may periodically pack the filling. Thus, in the course of an average day, the dispenser lever of a typical amalgam carrier will be depressed and released a multitude of times which weakens the leaf spring to eventually cause its fracture, oftentimes within a period of only six to twelve months. Replacement of the spring in a typical amalgam carrier sold by the assignee of the present invention requires removal of the pin which maintains the spring in proper position on the handle as well as securing the plunger to the handle. Pin removal is effected by means of drilling or driving it through the handle, both involving practices which are sufficiently time-consuming and damaging to the handle to justify replacing the entire amalgam carrier.

Further, even if the pin is successfully removed without damage to the handle or component parts, reassembly of the barrel, plunger, lever, spring and pin requires digital dexterity and patience.

The present invention provides an amalgam carrier wherein the barrel and spring lever are readily replaceable on the handle. The plunger is press-fitted or shrink-fitted into the handle and is not intended to be removed or replaced. The spring lever is unitary and may easily be screwed or pinned to the handle. Further, the spring lever member, now unitary, may be continuously depressed and released over extended periods of time without fracturing.

The barrel member is preferably polyvinylidene fluoride, suitably Kynar, a trademark product of Pennwalt Corporation, Philadelphia, Pennsylvania, assignee of the present invention. Kynar may be repeatedly successfully autoclaved and possesses a surface finish which resists retention of amalgam or restorative material better than the currently employed stainless steel barrels. Additionally, Kynar is receptive to color treatment enabling the barrel to be color-coded or color impregnated for the convenience of the dentist.

BRIEF DESCRIPTION OF THE DRAWINGS

FIG. 4 is a side elevational view of a portion of the amalgam carrier of the present invention.

FIG. 5 is a side elevational view of the spring lever illustrated in FIG. 4.

FIG. 6 is a sectional view of the amalgam carrier of FIG. 4 taken along line 6—6 thereof.

FIG. 7 is a plan view of the unitary spring lever member of FIG. 5.

FIG. 8 is a longitudinal sectional view of a portion of the amalgam carrier of FIG. 4.

DETAILED DESCRIPTION OF THE INVENTION

Figure 1:
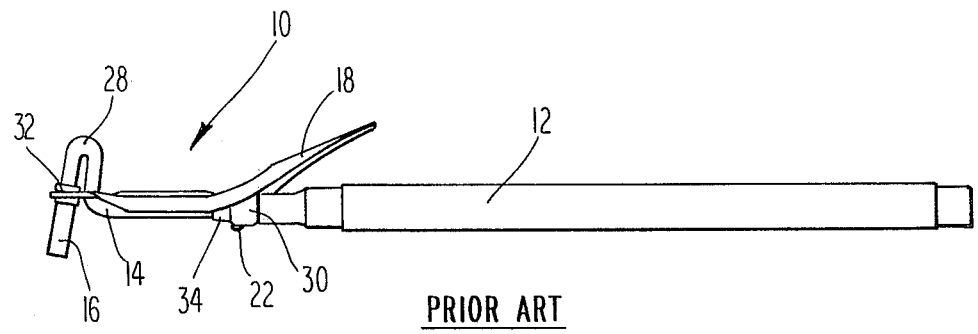
FIG. 1 is a side elevational view of a prior art amalgam carrier sold by the assignee of the present invention.

FIG. 1 illustrates a typical amalgam carrier sold by the assignee of the present invention. The amalgam carrier includes an amalgam tip 10 secured to handle 12. Tip 10 comprises a plunger 14, an open-ended barrel 16, dispensing lever 18, leaf spring 20, and a pin 22 which rigidly secures the amalgam tip to the handle. Plunger 14 extends axially from handle 12 and is secured thereto by pin 22. Free end 26 (FIG. 2) of plunger 14 is slidably disposed within barrel 16 which carries the amalgam. Plunger 14 is provided with a loop or arcuate bend 28 in order that the amalgam from the barrel may be transferred into a patient's cavity at a convenient and comfortable angle by the dentist.

Barrel 16 is provided with an annular grove 32 which is engaged by a forward portion of lever 18. Thus, when lever 18 is depressed (FIG. 2), and barrel 16 held against a surface of a prepared cavity site, free end 26 is caused to slide through barrel 16 to eject or transfer a portion or all of the amalgam carried therein to the site. Spring 20 urges lever 18 to its original undepressed position upon release of finger pressure thereon. Thus, free end 26 of the plunger rod is slidably reciprocable within barrel 16 upon the repeated depressing and releasing of the dispensing lever.

Figure 2:
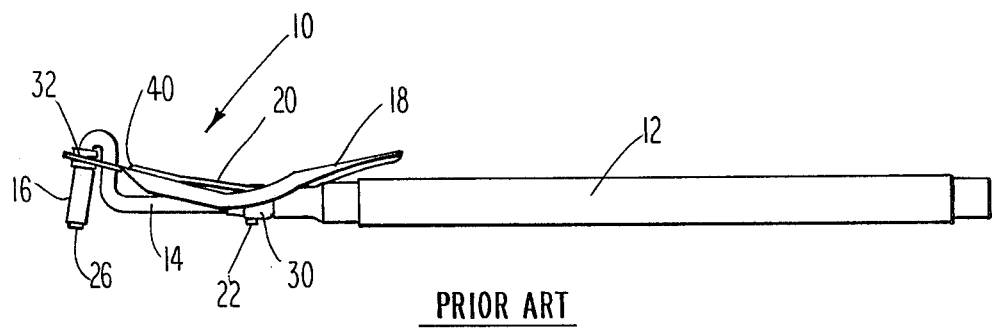
FIG. 2 is a side elevational view of the prior art amalgam carrier of FIG. 1 with dispensing lever in a depressed condition.

In FIG. 2, spring 20 is shown flexed while lever 18 is in a depressed postion. Free end 26 of the plunger has penetrated barrel 16.

Figure 3:
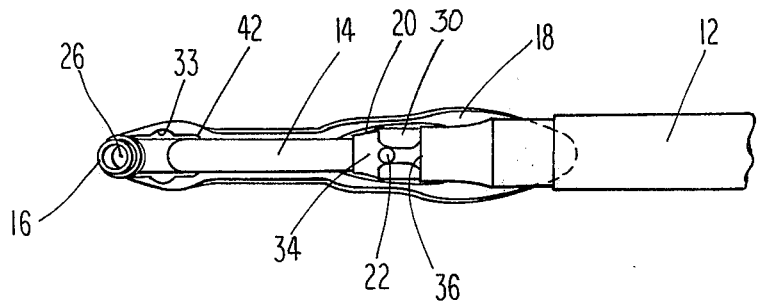
FIG. 3 is a perspective view of the underside of the amalgam tip portion of the carrier of FIG. 1.

In FIG. 3, spring 20 is affixed to handle 12 by means of snap clasp 30 engaging necked-down portion 34 of handle 12. Handle 12 is provided with an annular shoulder 36 against which snap clasp 30 abuts. Pin 22 is driven into aligned holes in necked-down portion 34 and plunger 14, and between clasp 30 to rigidly secure the assembled amalgam tip to the handle.

In FIGS. 4 through 8, spring lever 118 is an unitary member and replaces lever 18 and spring 20 in the embodiments of the prior art carriers shown in FIGS. 1, 2 and 3, and thus eliminates the long-standing problem of annoying and costly carrier breakdowns caused by spring fractures. Further, replacement of the amalgam tip is now a relatively simple procedure, later described.

Plunger 114 is made integral with handle 112 by means of a press-fit or shrink-fit therebetween (FIG. 8). Barrel 116 is similar to, and functions in an identical manner with barrel 16, but preferably comprises Kynar rather than stainless steel, reasons abovementioned.

Depressing spring lever 118 causes the free end of plunger 114 to slide through barrel 116 when the open or transferring end of barrel 116 is contacting a cavity surface to thereby eject or transfer a portion or all of the amalgam contained therewithin to the cavity.

Spring lever 118 comprises a forward portion 142 (FIG. 7) which engages annular groove 132 provided around barrel 116. Thus, as spring lever 118 is depressed, the free end of plunger 114 passes through barrel 116 in a manner similar to the action of plunger 14 passing through barrel 16 of prior art carriers.

Spring lever 118 further comprises a resilient member 144 having a longitudinally disposed slot 146 therein which receives screw 148 to permit the spring lever to be adjustably secured to handle 112. Resilient member 144 is disposed at an angle of about 5° (FIG. 5) to the main body of the spring lever in order that the spring lever will be urged to its undepressed postion upon release of finger pressure thereon.

FIG. 6 illustrates a typical cross-section of the spring lever at a point approximately midway between the barrel and forward end of the handle.

In assembling or replacing the amalgam tip of the present amalgam carrier, or any component thereof, plunger 114 is press-fitted or shrink-fitted into handle 112. Barrel 116 is frictionally engaged over the free end of plunger 114. Forward portion 142 of the spring lever is then caused to engage annular groove 132 of barrel 116 by passing the upper end of the barrel through enlarged opening 150 formed immediately rearwardly forward portion 142. Screw 148 may now be inserted in slot 146 and screwed into the handle to secure the spring lever thereto. The entire spring lever may be moved longitudinally along slot 146 in order to insure proper engagement of the barrel with forward portion 142.

In contrast therewith, in assembling amalgam tip 10 of the prior art amalgam carrier to handle 12, barrel 16 will be slid onto free end 26 of plunger 14. A forward portion of lever 18 engages annular groove 32 of barrel 16 by passing the upper end of the barrel through enlarged opening 33 (FIG. 3) provided in lever 18. Spring snap clasps 30 are then slid over necked-down portion 34 of handle 12 until the clasps abut shoulder 36. Pin 22 is now driven between clasps 30 (FIG. 3) and into aligned holes (not shown) in necked-down portion 34 and plunger 14. Lip 40 (FIG. 2) is then caused to engage opening 42 (FIG. 3) provided in lever 18 rearwardly opening 33.

Pinning the prior art amalgam tip assembly 10 requires the proper positioning of each component and, as aforementioned, demands digital dexterity and patience. In an attempt to make the spring more replaceable, screw means were employed in lieu of pin 22. The inordinate amount of time consumed in maintaining the components in proper position and alignment while struggling to insert and turn the screw militated against such a substitution. No such problem exists in assembling the amalgam tip of the present invention. Further, since the spring lever 18 rarely needs replacement, pin means may be substituted for screw 148.

I claim:
1. A dental amalgam carrier comprising
an open-ended barrel member for carrying said amalgam,
a cylindrical handle,
a plunger rod having one end extending axially rigidly from a first end of said handle, free end of said plunger rod slidable within said barrel member,
a spring lever adjustably mounted to said handle adjacent said first end thereof in longitudinal alignment therewith, said spring lever having an opening at a forward portion thereof for engaging said barrel while said barrel is carrying said free end of said plunger rod therein,
said spring lever comprising an unitary member devoid of separate spring means coacting therewith such that depression of said spring lever causes said free end of said plunger rod to transfer amalgam from said barrel member, and said spring lever returns to its undepressed position.

2. In a dental amalgam carrier comprising a cylindrical handle, an open-ended barrel for carrying said amalgam, and a plunger rod communicating between said barrel and handle, said plunger rod having one end pinned to a first end of said handle by pin means and its free end movable through said barrel when a dispensing lever engaging said barrel is depressed to thereby pivot said lever about a point intermediate its ends and substantially centrally therebetween, and separate spring means affixed to said first end of said handle and maintained in fixed position on said handle by said pin means, said spring means urging said lever to its undepressed position, the improvement to said carrier comprising
means for eliminating said spring means and pin means comprising
an unitary spring lever member having a resilient rear portion adjustably mounted to said handle adjacent said first end thereof, and a forward portion for engaging said barrel whereby depressing said spring lever causes said plunger rod to travel through said barrel, and
said plunger rod being integral with and non-removable from said first end of said handle.

3. A dental amalgam carrier characterized by absence of separate spring means for returning amalgam dispensing lever to its original undepressed position, said carrier comprising
an open-ended barrel member for carrying said amalgam,
a cylindrical handle,
a plunger rod having one end integral with and non-removable from a first end of said handle and extending axially therefrom, free end of said plunger rod slidable within said barrel, said plunger rod forming an open loop such that path of said reciprocable movement of said free end within said barrel member forms an oblique angle to axis of said handle,
a spring lever adjustably mounted to said handle adjacent said first end thereof in longitudinal alignment therewith, said spring lever having an opening at a forward portion thereof for engaging said barrel while said barrel is carrying said free end of said plunger therein,
said spring lever comprising an unitary member devoid of separate spring means coacting therewith such that depression of said spring lever causes said free end of said plunger rod to move at said oblique angle to axis of said handle while transferring amalgam from said barrel member, and said spring lever returns to its undepressed position.

4. The amalgam carrier of claim 1 wherein said plunger rod is force-fitted into said handle.

5. The amalgam carrier of claim 1 wherein said plunger rod is shrink-fitted into said handle.

6. The amalgam carrier of claim 1 wherein said spring lever includes
a resilient rear portion provided with a longitudinal slot therein, said slot receiving screw means therethrough for adjustably mounting said spring lever to said handle, said resilient rear portion urging said spring lever to an undepressed position upon release of finger pressure thereon.

7. The amalgam carrier of claim 6 wherein said resilient rear portion forms an angle of about 5° with main body of said spring lever when said spring lever is disassembled from said handle.

8. The amalgam carrier of claim 1 wherein said barrel member comprises polyvinylidene fluoride.

* * * * *